United States Patent [19]

Wanchik et al.

[11] 4,370,976

[45] Feb. 1, 1983

[54] DYNAMIC FOAM ORTHOSIS

[75] Inventors: Joseph Wanchik, Harper Woods; Joseph M. Gabriele, Fenton, both of Mich.

[73] Assignee: Contour Fabricators, Inc., Grand Blanc, Mich.

[21] Appl. No.: 156,253

[22] Filed: Jun. 3, 1980

[51] Int. Cl.³ .............................................. A61F 5/10
[52] U.S. Cl. .................................................... 128/77
[58] Field of Search ................... 128/24, 26, 77, 83, 128/87 R, 88, 89 R, 90, 133, 165, 166; 2/16, 18

[56] References Cited

U.S. PATENT DOCUMENTS

| | | | |
|---|---|---|---|
| 1,708,757 | 4/1929 | Freileweh | 128/89 R |
| 2,561,863 | 7/1951 | Holm | 128/157 |
| 3,815,587 | 6/1974 | Guerrant | 128/77 |
| 3,903,878 | 9/1975 | Spann | 128/77 |
| 4,041,940 | 8/1977 | Frankel | 128/87 R |

FOREIGN PATENT DOCUMENTS 1325526  7/1963  France ............................. 128/89 R

OTHER PUBLICATIONS

*Adult Hemiplegia;* 2nd ed.; B. Bobath; ©1978; Spottiswoode Ballantyne, Ltd.

*Primary Examiner*—Richard J. Apley
*Assistant Examiner*—Carl Moy
*Attorney, Agent, or Firm*—Harness, Dickey & Pierce

[57] ABSTRACT

This disclosure relates to a device which may be used to provide active forces necessary to substitute for decreased or absent muscle function in various joints of the body and to help bring deformed or spastic muscles and joints back to normal configuration. Since the device is made from relatively soft, resilient foam, the forces needed to provide assistance to various muscles are inherent within the device itself. The device contains a contoured cavity which is anatomically designed to simulate normal joint and muscle positions.

4 Claims, 4 Drawing Figures

DYNAMIC FOAM ORTHOSIS

BACKGROUND AND SUMMARY OF THE INVENTION

The present invention pertains primarily to medical devices and more particularly to orthosis or splinting devices.

Generally, an orthosis or splinting device is a device used to straighten joints which have assumed abnormal positions due to decreased or absent muscle function. A large percentage of patients requiring such splinting are seen in acute care hospitals following surgery or trauma, subsequently as outpatients, or in rehabilitation centers. Dynamic or adjustable splints frequently are used to substitute for absent muscle power and to assist weak muscle power, as well as to prevent contractures, to maintain balance, to promote rest, or to mobilize specific joints. The splinting devices themselves may be required for skeletal substitution, such as to aid in fracture alignment, or to support bones and joints having pathology. They may also be used to provide muscle balance for paralyzed muscles or for divided tendons or muscles. For resting patients, splints may be used to promote wound healing of newly repaired structures, or to treat infection or relieve pain.

Dynamic splinting may generally be defined as the application on a moving part of a force which remains approximately constant as the part moves. Often it is called "active" splinting, referring to the mobility which the splint gives to the patient's joints with specific and directional controls, by providing forces which substitute for absent muscle power. This joint mobility can decrease adhesions, maintain joint function, and prevent ankylosis of the joint. In addition, this type of splinting has a physiological effect as well, for when the muscles are moving they pump away stagnant fluids which wash out the toxins and keep the tendons sliding and joints moving. Dynamic or active splinting provides constant force over a long period of time in contrast to strong, short-term pressure, similar to the principle an orthodontist uses in straightening teeth. For example, it has been found that several hours of light, steady tension is very often more successful than vigorous exercise for a few minutes, especially where contractures are present. Progressive alteration to a static splint can draw out a contracture and active dynamic splinting can aid in maintaining the correction.

In the past, it has been the general rule that a dynamic splint must contain a rigid base specifically made to fit the particular patient since it has almost always been thought that a splint that fits everyone fits no one. This static base of a dynamic splint is of primary importance in most conventional splinting and usually comprises a rigid base which is secured to the subject joint and which forms the foundation for various traction-type mechanisms which are used for tensioning the subject joint or joints. The static base of the splint provides foundation for proper (functional) alignment of joints, provides a foundation to which tractioning components may be attached, and also provides the foundation for a hinge joint. It may also be used to aid in the relaxation of any spastic muscle, to allow tissues to adapt to their new position, to protect newly repaired structures, to provide support for proximal parts for allowing increased function in distal joints or uninvolved parts, and to aid in positioning for edema control. However, it is well known that when one is constructing the static base of the splint, one must always remember that such immobilization leads to joint stiffness. This has always been one of the major drawbacks of this type of splint since once such joint stiffness has occurred, it is difficult to overcome. It has been found that it is much easier to prevent joint stiffness in the first place, than it is to overcome it once it has occurred. As will be explained in more detail hereinbelow, the present invention does not lead to such joint stiffness.

Typical of devices currently used by the medical profession include what are known as "outriggers". These devices contain a rigid support base such as that described above and have various tightening and tensioning mechanisms projecting therefrom which from time to time are adjusted to bring the abnormal joint back to a normal configuration. Such dynamic splints are typically very complex in design and constructed so as to provide specific traction with directional control. They utilize outriggers which must be very carefully and accurately placed and secured to the body of the splint since the stability and the maintenance of splint position is of prime importance. Needless to say, these outrigger devices are uncomfortable to the wearer and also require considerable attention from the skilled personnel monitoring the progress of the return of the joint to normal position.

In addition to the disadvantages of prior art orthosis or splinting devices referred to above, most devices currently used are relatively bulky and unattractive. Very often they are also uncomfortable and produce pressure sores during use. In addition, most such devices are difficult to position and even then, improper fitting is a problem in many cases since custom-making each and every device to fit each and every patient would be impossible due to the costs involved. Once positioned, most such prior art devices require almost constant monitoring to assure continued positive action, thus involving significant additional expense due to the necessity of the continued presence of skilled medical personnel.

Accordingly, it is a principle object of the present invention to provide a dynamic orthosis device which, in addition to being comfortable and easy to fit, automatically provides an active extension force which gradually decreases as the subject joint or joints assume a normal extended position.

In general, the dynamic foam orthosis of the present invention provides active forces necessary to substitute for decreased, absent, or abnormal muscle function in jointed portions of a body. It comprises a cellular foam base, a cellular foam cover, and at least one restraining strap means. The cellular foam base is contoured with a cavity adapted to mate with and partially support the body portion requiring substitute muscle forces. The cellular foam cover which is used in conjunction with the base is movable with respect to the base from a closed position in which it is in engagement with the base to an open position in which the contoured cavity of the base is exposed so as to allow the subject body portion to be placed therein. At least one restraining strap means is used for holding the cover in engagement with the base once the subject body portion has been placed in the contoured cavity of said base. Due to the properties and design of the resilient foam, the device of the present invention provides active forces on the subject body portion which automatically change as the position of the body portion changes.

Additional advantages and features of the present invention will become apparent from a reading of the detailed description of the preferred embodiment which makes reference to the following set of drawings in which:

DESCRIPTION OF THE PREFERRED EMBODIMENT

Figure 1:
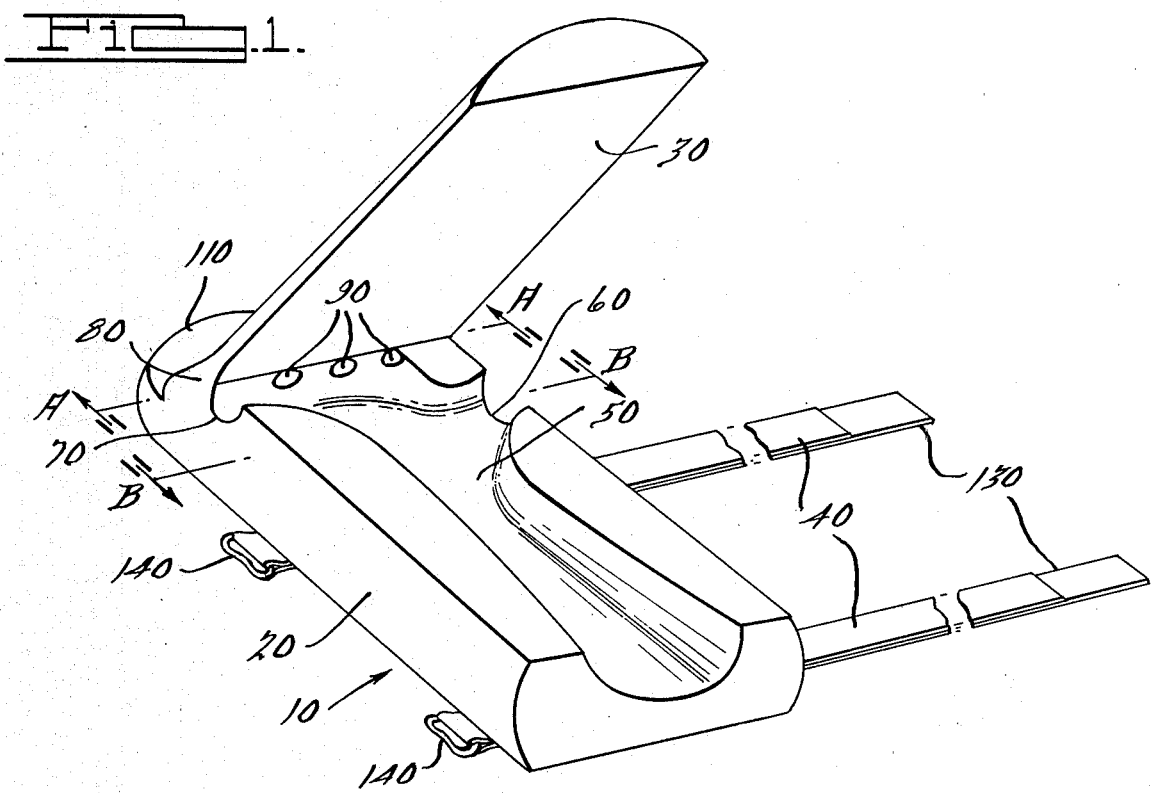
FIG. 1 is a perspective view of a preferred embodiment of the present invention, shown in an open position.
Figure 2:
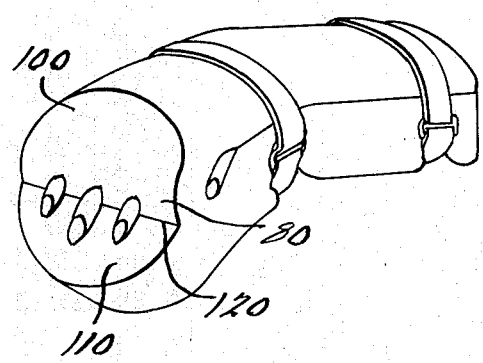
FIG. 2 is a perspective view of the present invention in a closed position and having a wrist and hand secured therein.

Referring now to the drawings, wherein the showings are for the purpose of illustrating a preferred embodiment of the present invention only and are not for the purpose of limiting the invention, FIG. 1 shows a dynamic foam orthosis or straightening device 10 made in accordance with the present invention comprising a cellular foam base 20, a cellular foam cover 30 integral with the base 20, and two restraining strap means 40 for use in holding the cover 30 in engagement with the base 20 once the patient's wrist and hand have been placed in the device. The base 20 is contoured with a cavity 50 on its upper surface which is designed to mate with and partially support a wrist, hand, and adjoining forearm which is placed within the cavity. The cavity shown in FIG. 1 is designed for a left hand, with the hand being placed in the cavity palm down, with the patient's thumb exiting the base through thumb opening 60, and the patient's small finger exiting the base through small finger opening 70. Along a hinge portion 80, where the cover 30 is joined to the base 20, three finger holes 90 are provided to allow for placement and separation of the patient's middle three fingers. As best seen in FIG. 2, the cover 30 is joined to the base 20 along the hinge portion 80, which is located along a slanted surface 100 which intersects the base 20 at its forward end to meet with finger support surface 110.

Figure 3:
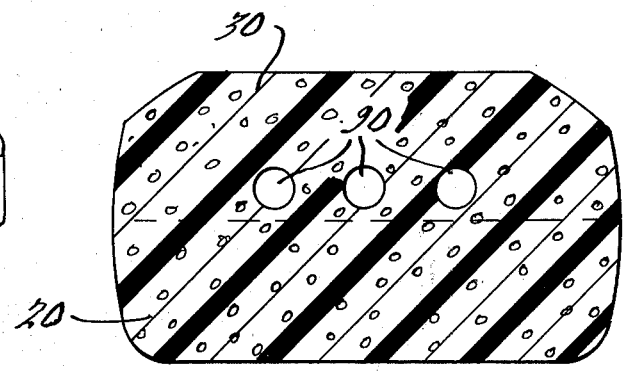
FIG. 3 is a view along the line A—A of FIG. 1.
Figure 4:
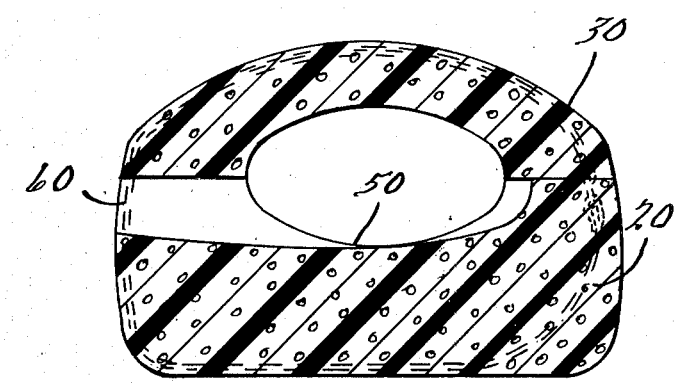
FIG. 4 is a view along the line B—B of FIG. 1.

With regard to one specific preferred embodiment of the present invention, and using FIG. 1 as representative, it has been found that using a cellular foam base 20 and integral cellular foam cover 30 made of relatively high resiliency polyurethane foam provides good support properties as well as comfort. A base about 15 inches long, about 7 inches wide, and about 2½ inches high, integrally connected to a cover which is rounded on its top surface, flat on its bottom surface, and about 2 inches high in the center of the arc of the rounded top surface, has been found satisfactory. The finger support surface 110 on the front end of the base 20 extends about 2¼ inches back from the forwardmost edge of the device to a break line 120 where it intersects the slanted surface 100 at an angle of about 45 to 50 degrees in the normal undeformed condition of the foam. The contoured cavity 50 in this preferred embodiment corresponds roughly to the shape and depth of the lower half of a patient's left forearm, wrist, and hand and is approximately 1¾ inches deep at its rearwardmost edge and extends upward to a portion about 1¼ inches deep located roughly in the middle of the palm of the hand. The three holes 90 for the middle three fingers of the patient are each approximately ¾ inches in diameter, with the center hole being located roughly in the center of the device and the other two holes being centered about 1½ inches from either lateral edge of the orthosis or straightening device of the present invention. Reference may also be had to FIG. 3 in this connection. The thumb opening 60 is about 1½ inches wide by about ¾ inches deep at the outside edge of the device, and the small finger opening 70 is about ¾ inches wide by about ½ inch deep at its opposing outside edge. FIG. 4 shows the relationship between the contoured cavity 50, and thumb opening 60. In addition to the previously described dimensions, the cavity 50 is contoured so as to provide 10° of dorsiflexion (the normal anatomical configuration), as measured from a line connecting the elbow and wrist. Also, the spacing of the fingers and thumb is that of normal anatomical extension.

When it is desired to use the device of the present invention to rehabilitate a deformed or spastic hand, the hand would be placed palm down in the contoured cavity 50 of the base 20, with the middle three fingers being appropriately separated and extended through each of the finger holes 90. The thumb and small finger would also be appropriately located before the cover would be brought down on top of the hand, wrist, and forearm. The restraining strap means would then be used to secure the patient's arm in the device of the present invention and would be tightened to the extent of a firm wrapping, but not as tight to make the wearer uncomfortable. In cases of noticeable deformity of the hand or wrist, once the hand and wrist have been placed in the device, the entire device will take on a more or less deformed configuration, as shown in FIG. 2. Since the device is made from relatively flexible foam, it flexes with the arm away from its normal flat configuration as shown in FIG. 1 to a deformed configuration, though leaving the device intact. However, it has surprisingly been found that the inherent springiness or resistance to compression found in the resilient cellular foam used in the present invention automatically exerts a force on the deformed hand to cause it to return to a normal anatomical configuration. Unexpectedly, in some cases, such return to normalcy takes as little as two weeks and needless to say requires no special monitoring or periodic adjustment by skilled medical personnel as do the prior art devices described earlier.

The restraining strap means used in the present invention preferably comprises a cinch strap containing a hook and loop type fastening system. For example, "Velcro" brand VST cinch straps provide excellent results. In the dimensioned preferred embodiment described earlier, and as shown in FIG. 1, two restraining straps 40 may be used, one positioned about 1½ inches from the rear edge of the base and the other positioned about 7¼ inches from the rear edge of the device, measured to the center of the straps. Each strap is about 25½ inches long and about 1½ inches wide with the last 3½ inches of length 130 being hook type fastener, and the other 22 inches of the exposed side of the restraining strap being loop type fastener. A cinch loop 140 is positioned near the bottom of one side of the base on each strap. In securing the restraining strap means, the section 130 is first threaded through the cinch loop 140 and then doubled back on itself, pulled taught, and then pressed down so that the hooks and loops of the strap engage. It should of course be appreciated that other belt-type restraining strap systems such as those using buckles, may also be used and are well within the scope of the present invention.

The dynamic foam orthosis of the present invention as described above in connection with this preferred embodiment, and as equally applicable to other jointed portions of the body, is designed to encourage and maintain normal extension of the wrist, fingers and thumb joints, or other jointed portions of the body for that matter, as well as to prevent joint stiffness by maintaining a continuous dynamic force. The compression of the foam which occurs when the fingers and thumb joints, for example, assume a flexed position provide an extension force which gradually decreases as the joints assume an extended position. The elasticity of the foam which covers the dorsum of the wrist also provides an extension force on the wrist, when the joint is flexed. The spreading of the fingers and thumb, combined with the extension of the wrist, fingers and thumb produces a positioning of the hand which tends to decrease spasticity and flexor-synergies.

As referred to above, it should of course be appreciated that the dynamic foam orthosis of the present invention, in addition to use on right or left arms, is equally adaptable to other joints of the body such as those of the feet, knee, elbow, etc. Of course, appropriate modifications of the base, cover, restraining straps, and especially the contoured cavity would have to be made to accommodate sizes and such other joints. In any case, the unique contoured cavity in the base of the present invention makes it possible to provide a "one size fits all" splinting device, thus proving incorrect the general rule of splinting devices referred to earlier, that a splint that fits everyone, fits no one.

In addition to the above advantages, the dynamic foam orthosis of the present invention provides a soft and comfortable splinting device, the mere mention of which in the past would have indicated an inefficient splinting device. The cellular foam used in the present invention provides a softness and breathability which makes the device almost unnoticeable to the wearer. Also, the universal design and innate natural qualities of the foam allow the device to conform to most patients without fear of pressure sores or improper fitting.

While the above description constitutes the preferred embodiment of the present invention, it will be appreciated that the invention is susceptible to modification, variation and change without departing from the proper scope or fair meaning of the accompanying claims.

What is claimed is:

1. A device for use in providing active forces necessary to substitute for decreased, absent, or abnormal muscle function in a wrist and hand comprising:
   an unsupported, relatively resilient, cellular foam base contoured with a cavity adapted to mate with and partially support the subject wrist and hand and adjoining forearm, and wherein said base contains three holes therethrough to allow for placement of the patient's middle three fingers,
   an unsupported, relatively resilient, cellular foam cover formed integrally with said base and movable with respect to said base from a closed position in which said cover is in engagement with said base to an open position in which the contoured cavity of said base is exposed so as to allow the subject wrist and hand to be placed therein, and
   at least one restraining strap means for holding said cover in engagement with said base once the subject wrist and hand have been placed in the contoured cavity of said base,
   said device providing active forces on the subject wrist and hand which change as the position of the subject wrist and hand changes.

2. A device for use in providing active forces necessary to substitute for decreased, absent, or abnormal muscle function in a wrist and hand comprising:
   an unsupported, relatively resilient, cellular foam base contoured with a cavity adapted to mate with and partially support the subject wrist and hand and adjoining forearm, with the cavity in said base being contoured in shape and depth to correspond roughly to the shape of the lower half of the patient's forearm, wrist, and hand, and wherein said base contains three holes therethrough to allow for placement and separation of the patient's middle three fingers,
   an unsupported, relatively resilient, cellular foam cover formed integrally with said base and movable with respect to said base from a closed position in which said cover is in engagement with said base to an open position in which the contoured cavity of said base is exposed so as to allow the subject wrist and hand to be placed therein, and
   two restraining strap means for holding said cover in engagement with said base once the subject wrist and hand have been placed in the contoured cavity of said base, the first of said restraining strap means being positioned generally around the wrist joint area and the second being positioned generally around the forearm,
   said device providing active forces on the subject wrist and hand which change as the position of the subject wrist and hand changes.

3. The invention of claim 2 wherein said cellular foam base and said cellular foam cover are made of polyurethane foam.

4. The invention of claim 2 wherein each of said restraining strap means comprises a cinch strap containing a hook and loop type fastening system.

* * * * *